(12) United States Patent
Sielcken et al.

(10) Patent No.: US 6,232,262 B1
(45) Date of Patent: May 15, 2001

(54) CARBONYLATION CATALYST SYSTEM

(75) Inventors: Otto E. Sielcken, Sittard; Henk Oevering, Stein; Frank P. W. Agterberg, Susteren; Paulus F. A. Buijsen, Herkenbosch; Imre Toth, Geleen, all of (NL)

(73) Assignee: DSM N?V?, Heerlen (NL)

( * ) Notice: Subject to any disclaimer, the term of this patent is extended or adjusted under 35 U.S.C. 154(b) by 0 days.

(21) Appl. No.: 09/414,087

(22) Filed: Oct. 7, 1999

(30) Foreign Application Priority Data

Apr. 7, 1997 (EP) .................................. 97201038
Apr. 6, 1998 (WO) .................................. PCT/NL98/04069

(51) Int. Cl.[7] .............................. B01J 31/18; C07F 15/00; C07C 67/37
(52) U.S. Cl. .......................... 502/162; 556/136; 560/207
(58) Field of Search ........................... 502/162; 556/136; 568/15, 16, 207

(56) References Cited

U.S. PATENT DOCUMENTS

| | | | |
|---|---|---|---|
| 4,325,834 | * 4/1982 | Bartish et al. | ........ 252/429 |
| 4,818,810 | 4/1989 | Drent . | |
| 4,880,902 | 11/1989 | van Doorn et al. . | |
| 4,960,747 | 10/1990 | van Doorn et al. . | |
| 5,229,475 | 7/1993 | Drent . | |
| 5,330,952 | 7/1994 | Drent . | |
| 5,350,876 | 9/1994 | Drent et al. . | |

FOREIGN PATENT DOCUMENTS

| | | |
|---|---|---|
| 0 305 012 A2 | 3/1989 | (EP) . |
| 0 490 452 A2 | 6/1992 | (EP) . |
| 2 101 601 | 1/1983 | (GB) . |

OTHER PUBLICATIONS

CA:121:9504 abs of Chem Ber 127(3) pp 481–8 by Hessler et al, 1994.*
CA:119:194306 abs of Polyhedron by Broadwood–Strong et al 12(7) pp 721–9, 1993.*

* cited by examiner

Primary Examiner—Jean F. Vollano
(74) Attorney, Agent, or Firm—Pillsbury Winthrop LLP

(57) ABSTRACT

Catalyst system comprising a palladium compound, an acid compound having a pKa>2 measured in water of 18° C. and an non-symmetrical bidentate phosphorous ligand according to:

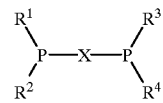

in which the —$PR^1R^2$ group is different from the —$PR^3R^4$ group and in which X is a divalent organic bridging group, in which the shortest direct link between the two phosphorous atoms in the bridging group X consists of a chain of 2–10 carbon atoms and optionally a sulphur or oxygen atom.

9 Claims, No Drawings

CARBONYLATION CATALYST SYSTEM

The invention relates to a novel catalyst system comprising a palladium compound, an acid compound having a pKa>2 measured in water of 18° C. and an non-symmetrical bidentate phosphorous ligand according to:

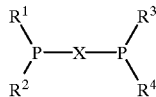

in which the —PR$^1$R$^2$ group is different from the —PR$^3$R$^4$ group, R$^1$–R$^4$ are organic groups and X is a divalent organic bridging group, in which the direct link between the two phosphorous atoms in the bridging group X consists of a chain of 2–10 carbon atoms and optionally a sulphur or oxygen atom.

In EP-A-273489 catalyst systems are described comprising palladium, a sterically hindered benzoic acid and a bidentate phosphine, i.e. 1,4-bis(diphenylphosphino) butane for use as catalyst in the carbonylation reaction of conjugated dienes and an alcohol to alkyl pentenoate compounds.

A disadvantage of this known catalyst composition is that the rate of reaction is relatively low when used as carbonylation catalyst. A need exists for a catalyst system which can increase the rate of this reaction (at a given temperature). Higher reaction rates also make it possible to operate at lower temperatures. This is advantageous because at lower temperatures less degradation of the catalyst system takes place. We have found that by using the catalyst system according to the invention the rate of the reaction can be improved considerably.

A catalyst system comprising palladium, an acid and non-symmetrical bidentate phosphine ligands, 1-(diisopropylphosphino)-1'-(phenylisopropylphosphino)-ferrocene is described in WO-A-9506027. This publication does not teach in any way that by using this non-symmetrical phosphine ligand higher reaction rates were to be expected. Moreover, only symmetrical phosphines were used in the examples. Furthermore it has been found that the disclosed catalyst system is less stable than the catalyst system according to the invention when used in a carbonylation reaction.

The non-symmetrical phosphine can be prepared by well known methods as for example described in GB-A-2101601.

Without being limited to the following theory it is believed that the improved reaction rate results from the fact that the electronic properties of the two phosphorous atoms of the ligand are different as a result of the different groups bonded to the phosphorous atoms. A larger difference in electronic properties of the two phosphorous atoms would result in a higher rate of reaction. Therefore it is preferred that one phosphorous atom is substituted with one or two electron withdrawing groups (R$^1$, R$^2$) while the other phosphorous atom is substituted with one or two electron donating groups (R$^3$, R$^4$). For example R$^1$, R$^2$ and R$^3$ can be electron withdrawing groups while R$^4$ is an electron donating group. This effect can also be achieved when for example R$^1$ and R$^2$ are one divalent organic group while R$^3$ and R$^4$ are both monovalent organic groups. More preferably one phosphorous atom is substituted with only electron withdrawing groups while the other phosphorous atom is only substituted with electron donating groups. Examples of electron withdrawing groups are aryl groups optionally substituted with —F, —Cl, —Br, —I, —CF$_3$, —SO$_3$H, —NR$^{3+}$, —NO$_2$, —ONO$_2$, —CO$_2$H, —CO$_2$R, —C(O)R, —NO and —ONO groups (R=C$_1$–C$_{28}$ alkyl group),or —O—R$^5$ groups, in which R$^5$ is preferably an aryl group optionally substituted with the above described groups.

Examples of electron donating groups are optionally substituted alkyl groups. Substituents of the alkyl groups is for example a —OR$^6$-group, in which R$^6$ is an C$_1$–C$_{28}$ alkyl group. Divalent cyclic alkylene groups are also examples of electron donating groups, provided that the number of C-atoms in the ring is equal or higher than 4.

Preferably optionally substituted C$_1$–C$_{10}$ alkyl groups are used as electron donating groups and optionally substituted C$_6$–C$_{10}$ aryl groups are used as electron withdrawing groups. Examples are methyl, ethyl, propyl, isopropyl, cyclopropyl, butyl, isobutyl, tert-butyl, cyclobutyl, pentyl, neopentyl, cyclopentyl, hexyl, cyclohexyl, heptyl, cycloheptyl, octyl, cyclooctyl, nonyl, decyl, 2-cyanoethyl, 2-hydroxyethyl, 2-dialkylaminoethyl, 2-bromomethyl, vinyl, allyl, crotyl, phenyl, o-tolyl, p-tolyl, 1-methoxyphenyl, 2-methoxyphenyl, 3-methoxyphenyl, 1-fluorophenyl, 2-fluorophenyl, 3-fluorophenyl, pentafluorphenyl, 2,3-dimethylphenyl, 2,4-dimethylphenyl, 2,5-dimethylphenyl, 2,6-dimethylphenyl, 3,5-dimethylphenyl, 2,4,6-trimethylphenyl, 1-cyanophenyl, 2-cyanophenyl, 3-cyanophenyl, 1-α, α, α-trifluorotolyl, 2-α, α, α-trifluorotolyl, 3-α, α, α-trifluorotolyl, naphthyl and benzyl. These alkyl groups and aryl groups are optionally (further) substituted with for example methyl, methoxy, cyanide or trifluoromethyl groups.

The bridging group X can be an organic group having between 2 and 20 carbon atoms with the proviso that the shortest direct link between the phosphorous atoms consists of 2 and 10 atoms. Preferably the direct link between the two phosphorous atoms in the bridging group X consists of a chain of 3–4 carbon atoms and optionally an additional non-terminal sulphur or oxygen atom.

Examples of possible non-symmetrical bidentate phosphine ligands are: 1-(diisopropylphosphino)-4-(diphenylphosphino)butane, 1-(dibutylphosphino)-4-(diphenylphosphino)butane, 1-(dicyclohexylphosphino)-4-(diphenylphosphino)butane, 1-(ditert-butylphosphino)-4-(diphenylphosphino)butane, 1-(tert-butylphenylphosphino)-4-(diphenylphosphino)butane, 1-(butylphenylphosphino)-4-(diphenylphosphino)butane, 1-(4,8-dimethyl-2-phosphabicyclo[3.3.1]nonane)-4-(diphenylphosphino) butane, 1-(9-bicyclo-phosphanonanyl)-4-(diphenylphosphino)butane, 1-(diisopropylphosphino)-3-(diphenylphosphino)propane, 1-(ditert-butylphosphino)-3-(diphenylphosphino)-propane or, 1-(cyclohexylphenylphosphino)-3- (diphenyl-phosphino)-propane.

The palladium can be present in the catalyst system in the form of a heterogeneous palladium compound or as a homogeneous palladium compound. Homogeneous systems are preferred. Since palladium forms complexes with the phosphine ligand, the choice of the initial Pd compound is in general not critical. Homogeneous palladium compounds include, for instance, palladium salts of, for instance, nitric acid, sulphonic acid, alkane carboxylic acids with not more than 12 carbon atoms or hydrogen halogenides (Cl, Br, I). Exemplary homogeneous palladium compounds include PdCl$_2$, PdBr$_2$, PdI$_2$, Na$_2$PdI$_4$, K$_2$PdI$_4$, PdCl$_2$(benzonitrile)$_2$ and bis(allylpalladium chloride). Another group of suitable halogen-free palladium compounds are palladium complexes such as palladium acetylacetonate (Pd(acac)$_2$), Pd(II) acetate, palladiumnitrate Pd(NO$_3$)$_2$, tris(tri-o-tolyl phosphine) palladium, and di-palladium-tris-(dibenzylideneacetone) (Pd$_2$(dba)$_3$). An exemplary of a heterogeneous palladium compound is a palladium compound on an ion exchanger such as, for example an ion exchanger containing carboxylic acid groups. Ion exchangers containing carboxylic acid groups are commercially available under the brand names Amberlite IRC 50® and Amberlite IRC 84® (Rohm & Haas). Another heterogeneous catalyst is an immobilized phosphine on carrier catalyst, in which the palladium forms complexes with the immobilized phosphine (phosphine being the ligand of the catalyst system). Carriers include polystyrene, polyacrylamide, silica, alumina, silica-alumina or zeolite support.

The acid compound with a pKa>2 is generally a protonic acid, preferably having a pKa between 2–6 measured in water at 18° C. Preferred acids are carboxylic acids having 1 to 30 carbon atoms. These carboxylic acids may be substituted with hydroxy, $C_1$–$C_4$ alkoxy groups, for example methoxy, amine or halogenide groups, for example Cl, I and Br. Exemplary carboxylic acids are benzoic acid, acetic acid, valeric acid, pentenoic acid, nonanoic acid and butanoic acid. The acid is preferably a sterically hindered carboxylic acid having a pKa of less than 4.5. Exemplary sterically hindered carboxylic acids are sterically hindered benzoic acids, for example 2-fluorobenzoic acid and 2-(trifluormethyl)-benzoic acid, the $C_1$–$C_4$ alkyl substituted benzoic acid, for example 2,6-dimethylbenzoic acid, 2-methylbenzoic acid, 2,4,6-trimethyl benzoic acid and hydroxy substituted benzoic acid, for example meta- and parahydroxybenzoic acid and other substituted benzoic acids, for example 2,6-difluorobenzoic acid or 2,4,6-tribromobenzoic acid. Most preferably 2,4,6-trimethylbenzoic acid is used.

The molar ratio of acid to palladium is preferably between 6:1 and 50:1 and more preferably between 10:1 and 40:1. It has been found that the optimum acid to palladium ratio depends on the specific carboxylic acid which is used.

The phosphine ligand to palladium molar ratio is as a rule between 1:1 and 100:1 and preferably between 2:1 and 10:1.

The palladium concentration in the reaction mixture is preferably as high as possible because the rate of the reaction per unit of reactor volume will then be higher. The upper limit for a homogeneous catalyst system will normally be determined by the solubility of palladium in the reaction mixture and will, for example, depend on the specific palladium compound used as discussed above. This upper limit can easily be determined by one skilled in the art. However, the process according to the invention may also be performed with a homogeneous catalyst system in the presence of additional solid palladium compounds.

The catalyst system according to the invention can be advantageously used as a carbonylation catalyst in a reaction of an olefinic organic compound, carbon monoxide and optionally a co-reactant. The olefinically unsaturated compound can be a $C_2$–$C_{20}$ organic compound, for example ethene, propene, butene, pentenes, hexenes and octenes. Preferably a conjugated diene, for example 1,3-pentadiene, 1,3-hexadiene and more preferably 1,3-butadiene is used. The co-reactant is preferably a nucleophilic compound having a mobile H-atom, for example water or a $C_1$–$C_{20}$ carboxylic acid. More preferably the co-reactant is an alcohol having between 1 and 20 carbon atoms. Examples of suitable alcohols are methanol, ethanol, propanol, isopropanol, n-butanol, tert-butanol, pentanol, cyclohexanol and phenol. Most preferably methanol and ethanol are used, for example because the resulting compounds can be advantageously be used as precursor to prepare nylon intermediates, like adipic acid and ε-caprolactam.

It has been found that this catalyst system according to the invention can also be advantageously used when converting 3-alkoxy-1-butene and/or 1-alkoxy-2-butene to the corresponding alkyl pentenoate. These compounds can be prepared from butadiene as for example described in EP-A-25240. The reaction conditions of the reaction from alkoxy butene to an alkyl pentenoate are generally the same as for the direct carbonylation of butadiene except that no additional alcohol is required as co-reactant.

The catalyst system can also be used as polymerization catalyst in processes to prepare polyketones by co-reacting unsaturated compounds with CO.

The molar ratio of co-reactant and butadiene in the reaction mixture may be between 0.1:1 and 10:1. In a continuous process it is preferred to keep this ratio between 0.5:1 and 3:1. More preferably this ratio is smaller than 1.5:1.

The molar ratio of conjugated diene and palladium can be between 0.01:1 and 1000:1. Preferably this ratio is between 10:1 and 300:1 and more preferably higher than 50:1.

The temperature during the carbonylation reaction is preferably between 25° C. and 200°C. The pressure is not particularly critical and generally ranges between 1 MPa and 100 MPa, although it is preferably greater than 2 MPa. An upper limit is not critical. A very high pressure is disadvantageous because the process equipment will become very expensive. A practical and preferred upper limit is therefore about 10 MPa.

The carbon monoxide can be used in a pure form or diluted with an inert gas such as, for example, nitrogen, rare gases or carbon dioxide. In general, more than 5% hydrogen is undesirable, since this can cause hydrogenation of the olefinic organic compound under the carbonylation conditions.

All inert solvents are in principle suitable as an additional solvent when using the catalyst system in a carbonylation reaction. It is also possible to use an excess of one of the reactants or (by-) products in such an amount that a suitable liquid phase is formed. Examples of (by-) products when reacting butadiene are $C_9$-esters and other high boiling by-products. Examples of inert solvents are sulphoxides and sulphones, such as for instance, dimethyl sulphoxide, diisopropyl sulphone; aromatic solvents, such as benzene, toluene, xylene; esters, such as methyl acetate, methyl valerate, pentenoate esters and butyrolactone; ketones, such as acetone or methylisobutyl ketone; ethers such as anisole, trioxanone, diphenyl ether and diisopropyl ether; and mixtures of these solvents. Preferably, diphenyl ether is used as additional solvent.

Preferably a continuous process is used. An example of reactor system for a continuous process is a series of continuously stirred tank reactors (CSTR) in which the catalyst system, a possible solvent, olefinic organic compound, optionally the co-reactant and carbon monoxide are fed to a first reactor. The various ratios according to the process of the invention can be maintained by controlling the feed rate of the various reactants and catalyst components.

The invention shall be elucidated by the following non-limiting examples.

EXAMPLE I

A 160 ml autoclave was filled with 0.133 grams (0.6 mmol) palladium acetylacetonate, 1.982 grams (1.2 mmol) 2,4,6-trimethylbenzoic acid and 3.0 mmol of a bidentate phosphine ligand (see Table 1). The autoclave was purged three times with nitrogen. Subsequently 75 ml water- and oxygen-free diphenylether was injected. The autoclave was purged three times with carbon monoxide before adjusting the pressure to 2.0 MPa with a CO atmosphere and subsequently the temperature was raised to 140° C. Immediately after reaching this temperature a mixture of 6.5 grams of butadiene, 4.0 grams methanol and 0.5 grams nonane (internal GC standard) was injected with CO into the autoclave. After injecting these starting compounds the pressure was adjusted to 5.0 MPa using CO. After the reaction time (see Table) the reaction mixture was analyzed by Gas Chromatography (GC). The results are presented in Table 1.

TABLE 1

| Example | ligand | reaction time (hours) | selectivity (a) (%) | conversion (%) | relative reaction rate (b) |
|---|---|---|---|---|---|
| I | 1-(di-isopropylphosphino)-4-(diphenylphosphino)butane | 1.5 | 86.1 | 87 | 1.75 |
| II | 1-(dibutylphosphino)-4-(diphenylphosphino)butane | 0.5 | 91.7 | 45 | 1.5 |
| III | 1-(butylphenylphosphino)-4-(diphenylphosphino)butane | 1.0 | 92.9 | 62 | 1.25 |
| IV | 1-(4,8-dimethyl-2-phosphabicyclo[3.3.1]nonanyl)-4-diphenylphosphino)butane | 1.5 | 89.9 | 81 | 1.43 |
| V | 1-(tert-butylphenyl-phosphino)-4-(diphenylphosphino)butane | 1 | 95.6 | 60 | 1.14 |
| comp A | 1,4-bis-(di-isopropyl-phosphino)-butane | 1.5 | 88.7 | 49 | 0.55 |
| comp B | 1,4-bis-(isopropylphenyl-phosphino)-butane | 0.75 | 90.0 | 32 | 0.63 |
| comp C | 1,4-bis-(diphenyl-phosphino)butane | 1.0 | 92.9 | 56 | 1 |

(a) selectivity to methyl pentenoate
(b) The reaction rates were normalized to the reaction rate of bis-(diphenylphosphino)butane (Comparative Experiment C; relative reaction rate = 1)

What is claimed is:

1. A catalyst system comprising a palladium compound, a protonic acid compound having a pKa between 2–6 measured in water of 18° C., and a non-symmetrical bidentate phosphorous ligand represented by the formula:

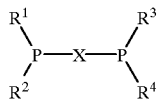

wherein the —$PR^1R^2$ group is different from the $PR^3R^4$ group, in which at least one of $R^1$ and $R^2$ is an electron-withdrawing group and at least one $R^3$ and $R^4$ is an electron-donating group, X is a divalent organic bridging group, in which the shortest direct link between the two phosphorous atoms in the bridging group X consists of a chain of 2–10 carbon atoms and optionally a sulphur or oxygen atom.

2. A catalyst system composition according to claim 1, wherein $R^1$ and $R^2$ are electron withdrawing groups and $R^3$ and $R^4$ are electron donating groups.

3. A catalyst system composition according to claim 2, wherein the electron withdrawing groups are substituted or non-substituted $C_6$–$C_{10}$ aryl groups and the electron donating groups are substituted or non-substituted $C_1$–$C_{10}$ alkyl groups.

4. A catalyst system according to claim 3, wherein $R^1$ and $R^2$ are aryl groups substituted with electron withdrawing groups.

5. A catalyst according to claim 1, wherein the direct link between the two phosphorous atoms in the bridging group X consists of a chain of three or four carbon atoms and optionally a nonterminal sulphur or oxygen atom.

6. A catalyst system according to claim 1, wherein the acid is a substituted benzoic acid.

7. A method for carbonylating an olefinic compound comprising conducting a carbonylation reaction of an olefinic organic compound, carbon monoxide and optionally a co-reactant using a catalyst system according to claim 1.

8. A method according to claim 7, wherein the olefinic compound is 1,3-butadiene and the co-reactant is a $C_1$–$C_{20}$ alcohol.

9. A method for forming an alkyl pentenoate comprising reacting an alkoxy butene with carbon monoxide in the presence of a catalyst system according to claim 1.

* * * * *